US008309108B2

(12) United States Patent
Watts et al.

(10) Patent No.: US 8,309,108 B2
(45) Date of Patent: Nov. 13, 2012

(54) INTRANASAL COMPOSITIONS

(75) Inventors: Peter Watts, Nottingham (GB); Yu-Hui Cheng, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 7 days.

(21) Appl. No.: 12/741,932

(22) PCT Filed: Nov. 10, 2008

(86) PCT No.: PCT/GB2008/003782
§ 371 (c)(1),
(2), (4) Date: Jun. 16, 2010

(87) PCT Pub. No.: WO2009/060226
PCT Pub. Date: May 14, 2009

(65) Prior Publication Data
US 2010/0249170 A1 Sep. 30, 2010

(30) Foreign Application Priority Data

Nov. 9, 2007 (EP) .................................. 07254426

(51) Int. Cl.
*A61K 9/00* (2006.01)
*A61P 25/16* (2006.01)
(52) U.S. Cl. ........................................ 424/400; 424/434
(58) Field of Classification Search .................. 424/400
See application file for complete search history.

(56) References Cited

U.S. PATENT DOCUMENTS

| 4,727,064 | A | 2/1988 | Pitha |
| 5,376,645 | A | 12/1994 | Stella et al. |
| 5,756,483 | A | 5/1998 | Merkus |
| 6,740,660 | B2 | 5/2004 | Achari et al. |

FOREIGN PATENT DOCUMENTS

| EP | 0834308 A1 | 4/1998 |
| WO | 9422445 A2 | 10/1994 |
| WO | 9605810 A1 | 2/1996 |
| WO | 9901498 A1 | 1/1999 |
| WO | 9927905 A1 | 6/1999 |
| WO | 2004062561 A2 | 7/2004 |
| WO | 2005079749 A2 | 9/2005 |

OTHER PUBLICATIONS

Park et al. In situ gelling and mucoadhesive polymer vehicles for controlled intranasal delivery of plasmid DNA. J Biomed Mater Res. Jan. 2002;59(1):144-51.*
Ugwoke et al., "Bioavailability of apomorphine following intranasal administration of mucoadhesive drug delivery systems in rabbits," Eur J Pharm Sci., vol. 9, 1999, pp. 213-219.
European Pharmacopoeia, 5th Edition, vol. 2, 2005, pp. 2264.
Chiappetta et al., "Poly(ethylene oxide)-ply(propylene oxide) block copolymer micelles as drug delivery agents: Improved hydrosolubility, stability and bioavailability of drugs," European Journal of Pharmaceutics and Biopharmaceutics, 66, 2007, pp. 303-317.
Holappa et al., "Novel Water-Soluble Quaternary Piperazine Derivatives of Chitosan: Synthesis and Characterization," Macromol. Biosci., 2006, 6, pp. 139-144.
Bernkop-Schnurch et al., "Thiolated polymers-thiomers: synthesis and in vitro evaluation of chitosan-2-iminothiolane conjugates," International Journal of Pharmaceutics 260, 2003, pp. 297-237.
Thanou et al., "N-Trimethylated Chitosan Chloride (TMC) Improves the Intestinal Permeation of the Peptide Drug Buserelin In Vitro (Caco-2 Cells) and In Vivo (Rats)," Pharmaceutical Research, vol. 17, No. 1, 2000, pp. 27-31.
Thanou et al., "Mono-N-Carboxymethyl Chitosan (MCC), a Polyampholytic Chitosan Derivative, Enhances the Intestinal Absorption of Low Molecular Weight Heparin Across Intestinal Ephithelia in Vitro and In Vivo," Journal of Pharmaceutical Sciences, vol. 90, No. 1, Jan. 2001, pp. 38-46.
Thompson, "Cyclodextrins—Enabling Excipients: Their Present and Future Use in Pharmaceuticals," Critical Reviews in Therapeutic Drug Carrier Systems, 14(1), 1997, pp. 1-104.
Rowe et al., "Poloxamer," Handbook of Pharmaceutical Excipients, American Pharmacists Association, Washington, 2006, pp. 535-538.
Munoz et al., "Long-Term Treatment With Intermitent Intranasal or Subcutaneous Aporrmorphine in Patients With Levodopa-Related Motor Fluctuations," Clinical Neuropharmacology, vol. 20, No. 3, 1997, pp. 245-252.
Van Laar et al., "Intranasal Apomorphine in Parkinsonian On-Off Fluctuations," Arch Neurol, vol. 49, May 1992, pp. 482-484.
Dewey et al., "A Double-Blind, Placebo-Controlled Study of Intranasal Apomorphine Spray as a Rescue Agent for Off-States in Parkinson's Disease," Movement Disorders, vol. 13, No. 5, 1998, pp. 782-787.
International Preliminary Report on Patentability and Written Opinion issued on May 11, 2010 in International Application No. PCT/GB2008/003782.
International Search Report issued on Feb. 10, 2009 in International Application No. PCT/GB2008/003782.
Office Action issued Dec. 20, 2010 in EP Appln. 08847366.5.
Office Action issued Jan. 25, 2011 in NZ Application No. 585107.
Office Action issued Jun. 1, 2011 in CN Application No. 200880115432.X.

(Continued)

*Primary Examiner* — David J Blanchard
*Assistant Examiner* — Devang Thakor
(74) *Attorney, Agent, or Firm* — Panitch Schwarze Belisario & Nadel LLP

(57) ABSTRACT

A liquid aqueous formulation for the intranasal administration of apomorphine includes:
(a) at least about 15 mg/ml of apomorphine; and
(b) a solubilising agent selected from
   (i) at least one polyoxyethylene-polyoxypropylene copolymer (poloxamer);
   (ii) at least one cyclodextrin; and
   (iii) at least one cyclodextrin together with chitosan.
The formulations of the invention can be used in the treatment or management of Parkinson's disease and erectile dysfunction.

12 Claims, No Drawings

OTHER PUBLICATIONS

Office Action issued Sep. 2, 2011 in EP Application No. 08847366.5.

Pre-grant Opposition filed Apr. 2, 2011 in IN Application No. 3234/DELNP/2010.

Notification of Grant of Patent Right for Invention issued Feb. 29, 2012 in CN Application No. 200880115432.X.

Notice of Intention to Grant Patent and Application as Amended issued Feb. 14, 2012 in EP Application No. 08847366.5.

Office Action issued May 3, 2012 in MX Application No. MX/E/2010/065060.

Examination Report and Notice of Acceptance of Complete Specification issued Apr. 26, 2012 in NZ Application No. 585107.

* cited by examiner

INTRANASAL COMPOSITIONS

CROSS-REFERENCE TO RELATED APPLICATIONS

This application is a Section 371 of International Application No. PCT/GB2008/003782, filed Nov. 10, 2008, which was published in the English language on May 14, 2009, under International Publication No. WO 2009/060226 A1 and the disclosure of which is incorporated herein by reference in its entirety.

BACKGROUND OF THE INVENTION

This application relates to liquid pharmaceutical compositions for the intranasal administration of apomorphine.

Apomorphine (6aβ-aporphine-10,11-diol) (structure below) is a potent dopamine D1- and D2-receptor agonist used primarily in the management of Parkinson's Disease. The use of apomorphine for managing erectile dysfunction has also been reported. Oral bioavailability of apomorphine is low and for the treatment of Parkinson's disease the drug is administered by subcutaneous injection and may have to be given several times daily, typically at a dose in the range of from 1 to 10 mg of the hydrochloride salt, which is in the form of a hemihydrate. Multiple daily injections can be inconvenient to the patient and this can lead to compliance problems and alternative routes of administration may have advantages.

Chemical structure of apomorphine hydrochloride hemihydrate:

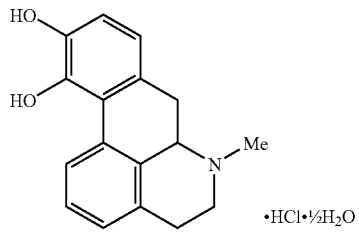

Formulations for intranasal administration of apomorphine have been reported elsewhere. For example, WO 99/27905 describes powder and solution formulations containing polymers designed to modify apomorphine absorption characteristics. Solution compositions for treating erectile dysfunction are described in U.S. Pat. No. 6,740,660. Powder compositions for treating Parkinson's disease are described in U.S. Pat. No. 5,756,483. Ugwoke et al (Eur J Pharm Sci., 9, 213-9, 1999) describe mucoadhesive apomorphine powder formulations containing Carbopol 971P and polycarbophil.

The listing or discussion of an apparently prior-published document in this specification should not necessarily be taken as an acknowledgement that the document is part of the state of the art or is common general knowledge.

Apomorphine is most commonly used in the hydrochloride salt form, which typically exists as a hemihydrate. As used herein the term "apomorphine" refers to the drug in non-salt or salt forms and in all states of hydration. Any reference to the amount of apomorphine in this document refers to the amount of apomorphine hydrochloride hemihydrate. Other salt forms of apomorphine which could be used in the present invention include, but are not limited to, mesilate, citrate, nitrate, lactate, maleate, tartrate, phosphate, succinate, fumarate and gluconate salts.

The saturated aqueous solubility of apomorphine hydrochloride is around 20 mg/ml at room temperature. In practice, it is not appropriate to prepare drug formulations in which the drug is present in an amount at or close to the saturated solubility of the drug. This is because there is a risk that the drug will precipitate out of solution unless the storage and usage conditions are very carefully controlled. Any precipitation or other change in the composition of the drug formulation would result in unreliable and/or variable amounts of drug being administered to patients on administration of a particular dosage volume. This has limited the use of the intranasal route for the delivery of apomorphine, particularly for the treatment/management of Parkinson's disease.

For intranasal delivery of a liquid formulation the maximum volume of liquid administered into each nostril should ideally not exceed 0.2 ml and be preferably 0.1 ml or less. Hence, using both nostrils and a solution containing 20 mg/ml apomorphine, the maximum achievable intranasal dose would be 8 mg.

Other problems associated with providing aqueous solutions of apomorphine include stability problems, particularly because apomorphine is highly susceptible to oxidation.

BRIEF SUMMARY OF THE INVENTION

The present invention seeks to address one or more of these problems and provides aqueous solutions comprising apomorphine for intranasal delivery. These solutions can be used to prevent, treat or manage any disease or condition for which apomorphine may be used, for example they can be used for the treatment and/or management of Parkinson's disease or erectile dysfunction.

The present invention provides a liquid aqueous formulation for the intranasal administration of apomorphine, which comprises:
  (a) at least about 15 mg/ml of apomorphine; and
  (b) a solubilising agent selected from
    (i) at least one polyoxyethylene-polyoxypropylene copolymer (poloxamer);
    (ii) at least one cyclodextrin; and
    (iii) at least one cyclodextrin together with chitosan.

In one aspect, the present invention provides aqueous liquid formulations comprising apomorphine in a concentration of at least 15 mg/ml and at least one polyoxyethylene-polyoxypropylene copolymer (poloxamer).

In another aspect, the present invention provides aqueous liquid formulations comprising apomorphine in a concentration of at least 15 mg/ml and at least one cyclodextrin.

In yet another aspect, the present invention provides a liquid aqueous formulation for the intranasal administration of apomorphine, which comprises at least 15 mg/ml of apomorphine and at least one cyclodextrin together with chitosan.

In still another aspect, the present invention also provides formulations as defined above for intranasal delivery for use in the prevention, treatment and/or management of diseases and conditions for which apomorphine is effective, including Parkinson's disease and erectile dysfunction.

In an additional aspect, the present invention provides a nasal drug delivery device or a dose cartridge for use in a nasal drug delivery device loaded with a formulation of the invention.

DETAILED DESCRIPTION OF THE INVENTION

The present invention provides a liquid aqueous formulation for the intranasal administration of apomorphine, which comprises:

(a) at least about 15 mg/ml of apomorphine; and
(b) a solubilising agent selected from
 (i) at least one polyoxyethylene-polyoxypropylene copolymer (poloxamer);
 (ii) at least one cyclodextrin; and
 (iii) at least one cyclodextrin together with chitosan.

The concentration of apomorphine in the formulations of the invention is at least about 15 mg/ml, for example from about 15 to about 100 mg/ml, more preferably at least about 20 mg/ml, for example from about 20 to about 80 mg/ml, more preferably at least about 25 mg/ml, for example from about 25 to about 60 mg/ml or from about 30 to about 50 mg/ml.

In a first aspect, the present invention provides aqueous liquid formulations comprising apomorphine in a concentration of at least 15 mg/ml and at least one polyoxyethylene-polyoxypropylene copolymer (poloxamer).

Poloxamers are block copolymers of ethylene oxide and propylene oxide and have the general formula $HO(C_2H_4O)_a(C_3H_6O)_b(C_2H_4O)_aH$, wherein a is typically from 2 to 130 and b is typically from 15 to 67. Preferably a is 90 or less and/or b is 40 or less.

Several different types of poloxamer are available commercially, from suppliers such as BASF, and vary with respect to the proportions of ethylene oxide "a" units and propylene oxide "b" units and molecular weight. There are five types of poloxamer which are currently used pharmaceutically and their details are summarised in the table below (European Pharmacopoeia 5.0, 2005, page 2264).

| Poloxamer type | Ethylene oxide units (a) | Propylene oxide units (b) | Content of oxyethylene (%) | Average molecular mass (Da) |
|---|---|---|---|---|
| 124 | 10-15 | 18-23 | 44.8-48.6 | 2090-2360 |
| 188 | 75-85 | 25-30 | 79.9-83.7 | 7680-9510 |
| 237 | 60-68 | 35-40 | 70.5-74.3 | 6840-8830 |
| 338 | 137-146 | 42-47 | 81.4-84.9 | 12700-17400 |
| 407 | 95-105 | 54-60 | 71.5-74.9 | 9840-14600 |

Surprisingly, it has been found that poloxamers can enhance the aqueous solubility of apomorphine to provide liquid formulations having a concentration of the drug as defined above and which have a viscosity suitable for administration using a nasal spray device.

Aqueous solutions of poloxamers undergo a temperature-dependent transition from solution to gel due to a reduction in solubility as temperature is increased. The temperature of this phase transition is highly dependent on the chemistry of the poloxamer, the concentration and the presence of other added ingredients such as salts. For example, an aqueous solution containing approximately 180 mg/ml or greater of poloxamer 407 will form a gel at ambient temperature and hence will be unsuitable for use in a nasal spray since it will be too viscous to be dispersed into droplets.

By the term "gel" we mean a semi-solid or solid preparation comprising organic macromolecules distributed uniformly throughout a liquid in such a way that no apparent boundaries exist between the dispersed macromolecules and the liquid.

The preferred poloxamers are those which when combined with apomorphine and the other ingredients needed to prepare a suitable intranasal formulation are not in the form of viscous solutions or gels at room temperature. Typically, such poloxamers have an average molecular mass of about 10,000 Da or less, e.g. about 9,700 Da or less. Especially preferred poloxamers for use in the invention are poloxamers 124, 188 and 237.

Surprisingly, it has been found that poloxamers 124, 188 and 237 can enhance the aqueous solubility of apomorphine to provide formulations having a concentration of the drug as defined above and which have a viscosity suitable for administration using a nasal spray device. Some other poloxamers such as poloxamer 407 typically provide formulations which are too viscous at room temperature to be suitable for use as nasal sprays.

The concentration of the poloxamer in the formulations of the invention is selected so that the solubility of the apomorphine is enhanced so that the formulations comprise apomorphine in an amount as defined above and so that the viscosity of the formulation is suitable for administration using a nasal spray device.

The concentration of poloxamer is preferably in the range of from about 10 to about 500 mg/ml, more preferably in the range of from about 20 to about 400 mg/ml and most preferably in the range of from about 30 to about 300 mg/ml, for example from about 50 to about 250 mg/ml.

Typically the viscosity of the poloxamer-containing formulations of the invention is 100 cps or less, preferably from about 1 about 40 cps, more preferably from about 2 to about 35 cps or from about 5 to about 30 cps, for example from about 10 to about 25 cps.

The poloxamers suitable for use in the invention typically provide both an enhancement in apomorphine solubility and solutions than can be dispersed into droplets when delivered at ambient temperature from a nasal spray device.

The droplet size of the poloxamer-containing formulations when delivered using a spray device and expressed as the volume mean diameter (D50%) is preferably from about 15 to about 500 μm, more preferably from about 20 to about 400 μm and most preferably from about 25 to about 350 μm, for example about 100 to 300 μm. D50% may be measured by a technique such as laser diffraction (e.g. SprayTec™ equipment, Malvern Instruments, UK).

Preferred formulations of the first aspect of the invention include solutions comprising:
 20 to 40 mg/ml apomorphine HCl, and
 100-200 mg/ml poloxamer 188. These solutions may also comprise a preservative and/or an antioxidant and/or a buffer. The concentration of the apomorphine HCl may, for example, be up to about 36 mg/ml.

In a second aspect, the present invention provides aqueous liquid formulations comprising apomorphine in a concentration of at least 15 mg/ml and at least one cyclodextrin.

Cyclodextrins are oligosaccharides made up of glucopyranose units and produced by enzymatic degradation of starch. They are "bucketlike" or "conelike" toroid molecules with a rigid structure and a central cavity, the size of which varies according to the cyclodextrin type. The internal cavity of cyclodextrins is hydrophobic and may allow for the inclusion of lipophilic molecules, thus improving the aqueous solubility of poorly soluble drugs (Thompson, Crit. Rev. Ther. Drug Can. Sys., 14, 1-104, 1997).

The three major types of cyclodextrin (CD) are α, β and γ which comprise 6, 7 and 8 glucopyranose units respectively. To extend their usefulness as pharmaceutical excipients, CDs, in particular β-CD, have been chemically modified, for example to produce derivatives that have enhanced aqueous solubility. Such derivatives include but are not limited to carboxymethyl-β-CD, carboxymethyl-ethyl-β-CD, diethyl-β-CD, methyl-β-CD, trimethyl-β-CD, randomly methylated β-CD, glucosyl-β-CD, maltosyl-β-CD, hydroxyethyl-β-CD, 2-hydroxypropyl-β-CD and sulfoalkyl ether-β-CDs, such as sulfobutyl ether-β-CD. As used herein, the term cyclodextrin includes derivatives of cyclodextrins such as those described above as well as underivatised cyclodextrins.

Especially preferred cyclodextrins for use in this invention are sulfoalkyl ether-β-CDs, for example sulfo $C_{2-6}$ alkyl ether-β-CDs, particularly sulfobutyl ether-β-cyclodextrin (SBE-β-CD). Suitable sulfoalkyl ether-β-CDs are described in U.S. Pat. No. 5,376,645, the contents of which are incorporated herein by reference. It has been found that these cyclodextrins aid the dissolution of apomorphine and have been found to provide solutions with excellent apomorphine stability and are well tolerated when administered intranasally.

The concentration of the cyclodextrin, for example a sulfoalkyl ether-β-CD such as SBE-β-CD is preferably in the range of from about 40 to about 500 mg/ml, more preferably in the range of from about 60 to about 400 mg/ml and most preferably in the range of from about 80 to about 300 mg/ml, for example of from about 100 to about 200 mg/ml.

Preferred formulations of the second aspect of the invention include solutions comprising:

20 to 50 mg/ml apomorphine HCl, and
100 to 150 mg/ml sulfobutylether-β-cyclodextrin. These solutions may also comprise a preservative and/or antioxidant and/or a buffer.

The cyclodextrin-containing apomorphine formulations may optionally also contain chitosan.

Thus, in a third aspect, the present invention provides a liquid aqueous formulation for the intranasal administration of apomorphine, which comprises at least 15 mg/ml of apomorphine and at least one cyclodextrin together with chitosan.

Chitosan is a bioadhesive cationic biopolymer comprising glucosamine and N-acetyl glucosamine. It is prepared by the deacetylation of chitin. In accordance with the present invention, the degree of deacetylation, which represents the proportion of N-acetyl groups which have been removed through deacetylation, should preferably be in the range of from about 40 to about 97%, more preferably be in the range of from about 60 to about 96% and most preferably be in the range of from about 70 to about 95%. The chitosan should preferably have a molecular weight in the range of from about 10,000 to about 1,000,000 Da, more preferably in the range of from about 30,000 to about 800,000 Da and most preferably in the range of from about 50,000 to about 600,000 Da.

By the term "chitosan" we include all derivatives of chitin, or poly-N-acetyl-D-glucosamine, including all polyglucosamines and oligomers of glucosamine materials of different molecular weights, in which the greater proportion of the N-acetyl groups has been removed through hydrolysis (deacetylation) and pharmaceutically acceptable organic and inorganic salts of chitosan. Suitable salts include, but are not limited to, nitrate, phosphate, acetate, hydrochloride, lactate, citrate or glutamate. Preferred salts are chitosan glutamate and chitosan hydrochloride. The most preferred salt is chitosan glutamate.

Chitosan derivatives and their salts are suitable for use in this invention. Chitosan derivatives may be prepared by bonding moieties to the hydroxyl or amino groups of chitosan and may confer the polymer with changes in properties such as solubility characteristics, charge density and mucoadhesiveness. For example, suitable chitosan derivatives prepared by bonding moieties to the hydroxyl groups of chitosan include esters, ethers or other derivatives formed by bonding acyl and/or alkyl groups with the hydroxyl groups. Examples include O-alkyl ethers of chitosan and O-acyl esters of chitosan. Other examples of chitosan derivatives include carboxymethyl chitosan (e.g. Thanou et al, J. Pharm. Sci., 90, 38-46, 2001), trimethylchitosan (e.g. Thanou et al, Pharm. Res., 17-27-31, 2000), thiolated chitosans (e.g. Bernkop-Schnurch et al, Int. J. Pharm., 260, 229-237, 2003) and piperazine derivatives (e.g. Holappa et al, Macromol. Biosci., 6, 139-144, 2006).

Chitosan derivatives for use in the invention also include those modified by conjugation with polyethylene glycol, for example as described in WO 99/01498. Suitable derivatives include those that are disclosed in Roberts, Chitin Chemistry, MacMillan Press Ltd., London (1992). The chitosans described in WO 96/05810 are also suitable for use in the present invention.

When chitosan is included in the formulations of the invention, the concentration of the chitosan is preferably in the range of from about 0.2 to about 25 mg/ml, more preferably in the range of from about 0.5 to about 20 mg/ml and most preferably in the range of from about 1 to about 15 mg/ml.

Chitosans suitable for use in the present invention may be obtained from various sources, including Primex, Iceland; NovaMatrix, Norway; Cognis, Germany; and Meron Biopolyomers, India.

Particularly preferred chitosan compounds that may be mentioned include chitosan glutamate (available as Protosan™ UPG 213 from NovaMatrix, Drammen, Norway).

The droplet size of the cyclodextrin-containing formulations when delivered using a spray device and expressed as the volume mean diameter (D50%) is preferably from about 15 to about 500 μm, more preferably from about 20 to about 400 μm and most preferably from about 25 to about 350 μm, for example about 35 μm for a formulation comprising SBE-β-CD or about 160 μm for a formulation comprising SBE-β-CD and chitosan. D50% may be measured by a technique such as laser diffraction (e.g. SprayTec™ equipment, Malvern Instruments, UK).

Apomorphine is highly susceptible to oxidation and the incorporation of one or more antioxidants into the formulations of the invention is preferred. Suitable antioxidants include ascorbic acid and its salts, ascorbyl palmitate, citric acid, erythorbic acid, fumaric acid, malic acid, monothioglycol, phosphoric acid, potassium metabisulfite, sodium metabisulfite, propionic acid, propyl gallate, edetic acid and its salts (e.g. disodium EDTA) and sodium sulfite. The preferred antioxidant is sodium metabisulfite and the concentration is preferably in the range of from about 0.1 to about 3 mg/ml, more preferably from about 0.2 to about 2.5 mg/ml and most preferably from about 0.3 to about 2 mg/ml.

The pH of the formulations of the invention is preferably in the range of from about 2.5 to about 5.5, more preferably from about 2.8 to about 5.0 and most preferably from about 3.0 to about 4.5, for example from about 3.3 to about 4.3.

A buffer may also be incorporated into the formulations of the invention in order to maintain a stable pH. Suitable buffers include phosphate, acetate, citrate and citrate-phosphate. The use of a buffer can be especially advantageous for some poloxamer-containing apomorphine solutions, where it has been found that there can be a tendency for the pH to drift upwards in the absence of buffer. Citrate and citrate-phosphate buffers are especially preferred since the citrate ions potentially provide additive antioxidant effects and hence enhance apomorphine stability. Methods for preparing citrate buffer and citrate-phosphate buffer include mixing appropriate volumes and concentrations of citric acid and sodium phosphate solutions or citric acid and sodium citrate solutions respectively.

We have also found that chitosan may act as a buffering agent in the apomorphine containing formulations when used as described above; for this purpose it could be used alone or in combination with buffer salts/conventional buffering agents.

To maintain microbiological quality, the formulations of the invention may also contain a preservative. Suitable preservatives include benzyl alcohol, potassium sorbate, parabens (e.g. methyl and propyl), phenylethyl alcohol, sodium benzoate, sorbic acid, benzethonium chloride and benzalkonium chloride. A preferred preservative is benzalkonium chloride. The concentration of preservative used in the formulations of the invention will depend on the nature of the preservative used. The person of ordinary skill in the art would be able to readily determine an appropriate concentration for a particular preservative. For example, if the preservative is benzalkonium chloride, the concentration of the preservative is preferably from about 0.05 to about 0.2 mg/ml.

Alternatively, preservatives may be omitted from the formulations, in which case the formulations can be kept free of microorganisms by making them aseptically or by terminally sterilising them.

Apomorphine is sensitive to oxygen. Therefore, preferred processes for making the formulations of the invention minimise contact between apomorphine and oxygen. An example of a preferred process is as follows:

Step 1: The dissolved oxygen content of water is minimised, any suitable known method may be used, for example boiling and cooling and/or sparging with an inert gas such as nitrogen or helium to produce water with a low oxygen content.

Step 2: The antioxidant(s) or other stabilisers, solubilising agent (poloxamer or cyclodextrin), chitosan (if used) and other optional ingredients such as buffering agents (typically prepared using water prepared according to Step 1 above) and preservative(s) are dissolved in the water.

Step 3: Drug is added and dissolved.

Step 4: The pH is adjusted as necessary and the formulation made up to final weight or volume with the water.

Step 5: The final solution is transferred to a container which is sealed under a blanket of nitrogen (nitrogen overfill).

The formulations of the invention may be administered to the nasal cavity in any suitable form, for example in the form of drops or as a spray. The preferred method of administration is as a spray, e.g. using a spray device. Spray devices can be single ("unit") dose or multiple dose systems, for example comprising a bottle, pump and actuator, and are available from various commercial sources, including Pfeiffer (Germany), Valois (France), Rexam (France) and Becton-Dickinson (USA).

Nasal spray devices of the types described above typically dispense up to 0.14 ml in a single actuation.

Typical nasal dosing regimens range from a single spray into one nostril to up to two sprays into each nostril.

The total liquid volume of solution delivered into the nasal cavity in one administration using the formulations of this invention is preferably from about 0.02 to about 1.0 ml, more preferably from about 0.03 to about 0.8 ml and most preferably from about 0.04 to about 0.6 ml, for example from about 0.05 to about 0.4 ml.

The spray pump may be assembled onto the bottle containing a formulation of the invention at the point of manufacture, preferably with a nitrogen overfill. Alternatively, the drug solution may be sealed into a glass bottle or vial (with nitrogen overfill) and provided in a pack with a separate nasal spray pump. The nasal spray pump may then be attached to the bottle at the point of use, for example by the pharmacist, patient or carer.

The present invention provides a nasal drug delivery device or a dose cartridge for use in a nasal drug delivery device loaded with a formulation of the invention.

The formulations of the invention can be used to treat and/or manage Parkinson's disease. They can also be used to treat other conditions for which apomorphine is known to be effective, such as erectile dysfunction. Thus, the present invention provides a method of administering apomorphine, to a patent in need thereof, for example for the treatment and/or management of Parkinson's Disease or erectile dysfunction, which comprises the intranasal administration of a formulation of the invention to the patient.

As used herein, we use the term "patient" to refer to both human and non-human animals. The invention is particularly suitable for use in the treatment of humans.

The present invention also provides the use of a poloxamer or a cyclodextrin or the combination of a cyclodextrin and chitosan in the manufacture of an aqueous formulation comprising apomorphine in an amount of defined above for intranasal administration to a patient in need of apomorphine. Such a medicament may be for the prevention, treatment and/or management of any disease or condition for which apomorphine is effective, including Parkinson's disease and erectile dysfunction.

The present invention also provides formulations as defined above for intranasal delivery for use in the prevention, treatment and/or management of diseases and conditions for which apomorphine is effective, including Parkinson's disease and erectile dysfunction.

The invention is illustrated by the following non-limiting Examples.

EXAMPLE 1

Preparation of Water for Making Intranasal Formulations 500 ml of water was dispensed into a 1 liter beaker. The water was heated to boiling point and boiled for 5 minutes. The beaker was then covered and the contents left to cool. Using 1 M hydrochloric acid solution, the pH of the water was adjusted into the range of from 3.5 to 4.0. The water was transferred to a bottle and the bottle tightly sealed with a lid. Just prior to be used for formulation preparation the water was purged with nitrogen for two minutes.

This water was used in Examples 2 to 5.

EXAMPLE 2

Solution Containing 35 mg/ml Apomorphine Hydrochloride, 200 mg/ml Poloxamer 188, 1 mg/ml Sodium Metabisulfite and 0.15 mg/ml Benzalkonium Chloride (Unbuffered)

10 g of poloxamer 188 (Lutrol™ F68, BASF, Germany) was weighed into a 50 ml beaker and approximately 40 ml of water (Example 1) added. The beaker contents were stirred until the poloxamer had dissolved. 1750 mg of apomorphine hydrochloride (MacFarlan Smith, Edinburgh, UK) was dispensed into a 50 ml volumetric flask. 1 ml of 50 mg/ml sodium metabisulfite (Riedel-de-Hän, Germany) aqueous solution was added to the flask followed by the poloxamer solution. The beaker was rinsed with a small amount of water and transferred to the flask. The flask contents were stirred and when the apomorphine had dissolved 0.5 ml of 15 mg/ml benzalkonium chloride (Molekula, Shaftsbury, UK) aqueous solution added. The solution pH was measured and adjusted to pH 3.5 to 4.0 using 1 M HCl solution. The flask contents were made up to volume with water (Example 1) and then transferred as 4.9 ml aliquots into injection vials. Each vial was overfilled with nitrogen and a stopper and aluminium overseal attached.

EXAMPLE 3

Solution Containing 50 mg/ml Apomorphine Hydrochloride, 150 mg/ml Sulfobutylether-β-CD (SBE-β-CD), 1 mg/ml Sodium Metabisulfite and 0.15 mg/ml Benzalkonium Chloride (Unbuffered)

7.5 g of SBE-β-CD (Captisol®, CyDex, Lenexa, KS, USA) was weighed into a 50 ml beaker and approximately 40 ml of water (Example 1) added. The beaker contents were stirred until the cyclodextrin had dissolved. 2.5 g of apomorphine hydrochloride was dispensed into a 50 ml volumetric flask. 1 ml of 50 mg/ml sodium metabisulfite aqueous solution was added to the flask followed by the cyclodextrin solution. The beaker was rinsed with a small amount of water which was transferred to the flask. The flask contents were stirred and when the apomorphine had dissolved 0.5 ml of 15 mg/ml benzalkonium chloride aqueous solution added. The solution pH was measured and adjusted to pH 3.5 to 4.0 using 1 M HCl solution. The flask contents were made up to volume with water (Example 1) and then transferred as 4.9 ml aliquots into injection vials. Each vial was overfilled with nitrogen and a stopper and aluminium overseal attached.

EXAMPLE 4

Solution Containing 50 mg/ml Apomorphine Hydrochloride, 150 mg/ml Sulfobutylether-β-CD (SBE-β-CD), 5 mg/ml Chitosan Glutamate, 1 mg/ml Sodium Metabisulfite and 0.15 mg/ml Benzalkonium Chloride 7.5 g of SBE-β-CD was weighed into a 50 ml beaker and approximately 40 ml of water (Example 1) added. The beaker contents were stirred until the cyclodextrin had dissolved. 250 mg of chitosan glutamate (Protasan™ UPG 213, Novamatrix, Drammen, Norway) was added to the cyclodextrin solution and the beaker contents stirred until dissolved. 2.5 g of apomorphine hydrochloride was dispensed into a 50 ml volumetric flask. 1 ml of 50 mg/ml sodium metabisulfite aqueous solution was added to the flask followed by the cyclodextrin/chitosan solution. The beaker was rinsed with a small amount of water which was transferred to the flask. The flask contents were stirred and when the apomorphine had dissolved 0.5 ml of 15 mg/ml benzalkonium chloride aqueous solution added. The solution pH was measured and adjusted to pH 3.5 to 4.0 using 1 M HCl solution. The flask contents were made up to volume with water (Example 1) and then transferred as 4.9 ml aliquots into injection vials. Each vial was overfilled with nitrogen and a stopper and aluminium overseal attached.

EXAMPLE 5

Stability of Apomorphine Solutions Prepared using Sulfobutylether-β-CD

A solution was prepared using sulfobutylether-β-cyclodextrin (SBE-CD, Table 1) and following the same procedures described in the earlier Examples. The solution contained 1 mg/ml sodium metabisulphite and 0.15 mg/ml benzalkonium chloride and was adjusted to pH 3.5-4.0. "Chitosan" in Table 1 refers to chitosan glutamate.

Samples were stored in sealed glass vials at 5° C., room temperature ("RT") (approximately 18-22° C.) and 40° C. and observations made at weekly intervals. All of the samples initially appeared as pale yellow solutions.

TABLE 1

Sulfobutylether-β-cyclodextrin solutions

| Formulation | Observations | | | |
|---|---|---|---|---|
| | Week 1 | Week 2 | Week 3 | Week 4 |
| 20 mg/ml APO 100 mg/ml SBE-β-CD | No change | No change | No change | No change |
| 20 mg/ml APO 150 mg/ml SBE-β-CD 5 mg/ml chitosan | No change | No change | No change | No change |
| 50 mg/ml APO 150 mg/ml SBE-β-CD | No change | No change | No change | No change |
| 50 mg/ml APO 150 mg/ml SBE-β-CD 5 mg/ml chitosan | No change | No change | No change | No change |

Degradation of apomorphine is associated with the solution turning green. The SBE-β-CD solutions remained visually unchanged which implied apomorphine was chemically and physically stable.

EXAMPLE 6

Preparation of Solutions for Making Buffers 0.1M citric acid solution: 10.5 g of citric acid monohydrate (Fisher Scientific, Loughborough, UK) was weighed into a 500 ml volumetric flask and dissolved in approximately 490 ml of boiled and cooled water. The solution was made up to volume with boiled and cooled water.

0.1M sodium citrate solution: 5.88 g of trisodium citrate dihydrate (Sigma) was weighed into a 200 ml volumetric flask and dissolved in approximately 190 ml of boiled and cooled water. The solution was made up to volume with water.

0.2M dibasic sodium phosphate solution: 3.56 g of disodium hydrogen orthophosphate dihydrate (dibasic sodium phosphate dihydrate) (Fisher Scientific) was weighed into a 100 ml volumetric flask and dissolved in approximately 90 ml boiled and cooled water. The solution was made up to volume with boiled and cooled water.

EXAMPLE 7

Buffered Solution Containing 35 mg/ml Apomorphine Hydrochloride, 200 mg/ml Poloxamer 188, 1 mg/ml Sodium Metabisulfite and 0.15 mg/ml Benzalkonium Chloride 165 ml of 0.1 M citric acid and 91 ml of 0.2 M dibasic sodium phosphate solution (Example 7) were mixed together to produce pH 3.8 citrate-phosphate (McIlvaine) buffer and purged with nitrogen for two minutes.

10 g of poloxamer 188 was weighed into a 50 ml beaker and approximately 35 ml of the citrate-phosphate buffer solution added. The beaker contents were stirred until the poloxamer had dissolved. 1750 mg of apomorphine hydrochloride was dispensed into a 50 ml volumetric flask. 1 ml of 50 mg/ml sodium metabisulfite aqueous solution was added to the flask followed by the poloxamer solution. The beaker was rinsed with a small amount of buffer solution and transferred to the flask. The flask contents were stirred and when the apomorphine had dissolved 0.5 ml of 15 mg/ml benzalkonium chloride aqueous solution added. The flask contents were made up to volume with buffer solution and then transferred as 2.5 ml aliquots into 3 ml injection vials. Each vial was overfilled with nitrogen and a stopper and aluminium overseal attached.

EXAMPLE 8

Buffered Solution Containing 35 mg/ml Apomorphine Hydrochloride, 150 mg/ml Sulfobutylether-β-CD, 1 mg/ml Sodium Metabisulfite and 0.15 mg/ml Benzalkonium Chloride 200 ml of 0.1 M citric acid (Example 7) was dispensed into a glass bottle and 0.1M sodium citrate solution (Example 7) added with stirring until pH 3.8 was reached. The resulting citrate buffer was purged with nitrogen for two minutes.

7.5 g of SBE-β-CD was weighed into a 50 ml beaker and approximately 40 ml of citrate buffer solution added. The beaker contents were stirred until the cyclodextrin had dissolved. 1750 mg of apomorphine hydrochloride was dispensed into a 50 ml volumetric flask. 1 ml of 50 mg/ml sodium metabisulfite aqueous solution was added to the flask followed by the cyclodextrin solution. The beaker was rinsed with a small amount of buffer solution which was transferred to the flask. The flask contents were stirred and when the apomorphine had dissolved 0.5 ml of 15 mg/ml benzalkonium chloride aqueous solution added. The flask contents were made up to volume with buffer solution and then transferred as 2.5 ml aliquots into 3 ml injection vials. Each vial was overfilled with nitrogen and a stopper and aluminium overseal attached.

EXAMPLE 9

Solutions Containing 35 mg/ml Apomorphine Hydrochloride, 200 mg/ml Poloxamer, 11.44 mg/ml Citric Acid Monohydrate, 8.00 mg/ml Sodium Citrate Dihydrate, 1 mg/ml Sodium Metabisulfite and 0.15 mg/ml Benzalkonium Chloride 144 mg of citric acid monohydrate and 80 gm of sodium citrate dihydrate were weighed into a 25 ml beaker and approximately 5 ml of nitrogen-purged water was added. The beaker contents were stirred until the solids had dissolved to produce a buffer solution. 2 g of poloxamer 124 (Synperonic™ L44, Croda, France) was then transferred to the buffer solution and stirred until the poloxamer had dissolved. 0.1 ml of 100 mg/ml sodium metabisulfite solution was added to the beaker followed by 350 mg of apomorphine hydrochloride and the contents stirred until the drug had dissolved. Finally, 0.5 ml of 15 mg/ml benzalkonium chloride solution was added. The solution pH was measured and adjusted, if necessary, into the range pH 3.5-4.0 using 0.1M HCl or 0.1M NaOH solution. The beaker contents were then transferred into a 50 ml volumetric flask and made up to volume with nitrogen-purged water.

The above was repeated to produce solutions containing 200 mg/ml of poloxamers 188 (Lutrol F68, BASF), 237 (Pluronic™ F87, BASF), 338 (Pluronic™ F108, BASF) and 407 (Lutrol™ F127, BASF).

The viscosity of each solution was measured using a Brookfield Instruments cone and plate viscometer.

2.5 ml of each solution was transferred into each of two 5 ml glass bottles and a Pfeiffer multi-dose nasal spray pump (0.1 ml spray volume) attached. The spray pump was primed by actuating 5 times. The primed spray bottle was transferred into an Innova™ NSP actuator station (Innova Instruments, NJ, USA). This equipment was integrated into a Malvern SprayTec™ particle analyser (Malvern Instruments, Malvern, UK). The spray bottle was actuated and the droplet size distribution of each solution was measured. This was repeated two more times to provide a total of three readings for each bottle.

The table below provides viscosity and mean droplet size data for the apomorphine solutions containing the different types of poloxamer. A qualitative assessment of the spray plume is also provided.

| Poloxamer type | Viscosity of solution (cp) | Droplet size (μm) | | | Appearance of spray plume |
|---|---|---|---|---|---|
| | | D10% | D50% | D90% | |
| 124 | 6.1 | 21 | 54 | 225 | ++++ |
| 188 | 17.6 | 65 | 179 | 354 | +++ |
| 237 | 17.5 | 69 | 195 | 368 | +++ |
| 338 | 56.3 | 108 | 320 | 437 | + |
| 407 | 161.3 | 118 | 349 | 449 | + |

+++++ = Excellent spray plume - broad, well-dispersed cloud of droplets
+ = Narrow, jet-like spray The data show that the droplet size increases as solution viscosity increases. Solutions containing poloxamers 124, 188 and 237 were considered to have acceptable spray properties. Poloxamers 338 and 407 produced a narrow, jet-like spray and were considered to be less suitable for intranasal administration.

EXAMPLE 10

Buffered Solution Containing 36 mg/ml Apomorphine Hydrochloride, 200 mg/ml Poloxamer 188, 1 mg/ml Sodium Metabisulfite, 0.15 mg/ml Benzalkonium Chloride, 7 mg/ml Citric Acid Monohydrate, 4.5 mg/ml Sodium Citrate Dihydrate at pH 3.5-4.0

70 mg of citrate acid monohydrate and 45 mg of sodium citrate dihydrate were weighed and transferred into a 25 ml beaker and approximately 6 ml nitrogen-purged water added. The beaker contents were stirred until the solids had dissolved. 2 g of poloxamer 188 was weighed and added into the beaker and stirred until the poloxamer had dissolved. 0.1 ml of 100 mg/ml sodium metabisulfite aqueous solution was added to the beaker followed by 360 mg of apomorphine hydrochloride. The contents were stirred and when the apomorphine had dissolved 0.1 ml of 15 mg/ml benzalkonium chloride aqueous solution was added. The pH of the solution was measured and adjusted to 3.5-4.0 using either 1M HCl or 0.1M NaOH as necessary. The contents were transferred into a 10 ml volumetric flask and made up to volume with nitrogen-purged water.

EXAMPLE 11

Solution Containing 20 mg/ml Apomorphine Hydrochloride, 100 mg/ml Poloxamer, 7 mg/ml Citric Acid Monohydrate, 4.5 mg/ml Sodium Citrate Dihydrate, 1 mg/ml Sodium Metabisulfite and 0.15 mg/ml Benzalkonium Chloride 0.35 g of citric acid monohydrate and 0.225 g of sodium citrate dihydrate were weighed into a 100 ml beaker. Approximately 30 ml of nitrogen-purged water added to the beaker and the contents stirred until the solids had dissolved. 5 g of poloxamer 188 was added to the beaker contents and stirred until the poloxamer had dissolved. 0.5 ml of 100 mg/ml sodium metabisulfite solution was added to the beaker contents, followed by 1 g of apomorphine hydrochloride. The contents were then stirred until the drug had dissolved. Finally, 0.5 ml of 15 mg/ml benzalkonium chloride solution was added. The pH of the solution was measured and adjusted, if necessary, into the range pH 3.5-4.0 using 0.1M HCl or 0.1M NaOH solution. The beaker contents were transferred into a 50 ml volumetric flask and made up to volume with nitrogen-purged water.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A liquid aqueous formulation for the intranasal administration of apomorphine, which comprises:
   (a) at least about 15 mg/ml of apomorphine; and
   (b) a solubilising agent consisting essentially of at least one polyoxyethylene-polyoxypropylene copolymer (poloxamer) having an average molecular mass of from about 1,065 Da to about 9,700 Da, and a general formula $HO(C_2H_4O)_a(C_3H_6O)_b(C_2H_4O)_aH$, wherein a is from 2 to 90 and b is from 15 to 40;
   wherein the formulation does not contain a poloxamer of a type and in an amount resulting in a formulation too viscous to be dispersed into droplets at a temperature of 18° C. to 22° C.

2. A formulation according to claim 1, comprising at least about 20 mg/ml of apomorphine.

3. A formulation according to claim 2, comprising about 25 to about 60 mg/ml of apomorphine.

4. A formulation according to claim 1, wherein the poloxamer is poloxamer 124, poloxamer 188 or poloxamer 237.

5. A formulation according to claim 4, wherein the poloxamer is present in an amount of 50 to 250 mg/ml.

6. A formulation according to claim 4, which comprises 20 to 40 mg/ml apomorphine HCl and 100 to 200 mg/ml poloxamer 188.

7. A formulation according to claim 1 comprising an antioxidant.

8. A nasal drug delivery device or a dose cartridge for use in a nasal drug delivery device loaded with a formulation as defined in claim 1.

9. A method of administering apomorphine to a patient in need thereof, which method comprises the intranasal administration of a formulation as defined in claim 1.

10. A method according to claim 9, wherein the patient is suffering from Parkinson's disease and the intranasal administration treats or manages the Parkinson's disease.

11. A method according to claim 9, wherein the patient is suffering from erectile dysfunction and the intranasal administration treats or manages the erectile dysfunction.

12. A method of enhancing aqueous solubility of apomorphine, the method comprising mixing apomorphine with a solubilising agent, wherein the solubilising agent consists essentially of at least one polyoxyethylene-polyoxypropylene copolymer (poloxamer) having an average molecular mass of from about 1,065 Da to about 9,700 Da and a general formula $HO(C_2H_4O)_a(C_3H_6O)_b(C_2H_4O)_aH$; wherein a is from 2 to 90 and b is from 15 to 40; wherein the formulation does not contain a poloxamer of a type and in an amount resulting in a formulation too viscous to be dispersed into droplets at a temperature of 18° C. to 22° C.

* * * * *